United States Patent [19]
Brandely et al.

[11] Patent Number: 5,108,743
[45] Date of Patent: Apr. 28, 1992

[54] METHOD OF TREATING PRIMARY CANCERS OF THE PLEURA

[75] Inventors: Maud Brandely; Danielle Lando, both of Paris, France

[73] Assignee: Roussel Uclaf, Paris, France

[21] Appl. No.: 605,986

[22] Filed: Oct. 30, 1990

[30] Foreign Application Priority Data

Nov. 10, 1989 [FR] France ................................ 89 14780

[51] Int. Cl.$^5$ .............................................. A61K 37/66
[52] U.S. Cl. ..................................... 424/85.5; 424/85.4
[58] Field of Search ............................... 424/85.5, 85.4

[56] References Cited

FOREIGN PATENT DOCUMENTS 8705518 9/1987 PCT Int'l Appl. ................ 424/85.5

OTHER PUBLICATIONS

Vadhan-Raj et al. (1986) J. Clin. Oncol. 4(2):137–146.
D'Acquisto et al (1988) J. Clin. Oncol. 6(4):689–695.
van der Burg et al. (1985) J. Biol. Response Modifiers 4:264–272.
Welander et al. (1988) Am. J. Clin. Oncol. 11(4):465–469.
Boutin, (1990, Mar.) Bull. Acad. Natl. Med. 174(3):421–426, (abstract only).
Boutin et al. (1990) Rev. Pneumol Clin. 46(5):211–215, (abstract only).
Cox et al. (Mar., 1986), Phase 1 trial of subcutaneous recombinant DNA gamma interferon, Proceedings of Am. Assoc. of Cancer Res. 27:191, Abstract #756.

Primary Examiner—Robert A. Wax
Assistant Examiner—Richard C. Ekstrom
Attorney, Agent, or Firm—Bierman and Muserlian

[57] ABSTRACT

A method of treating primary cancers of pleura in warm-blooded animals having said cancers comprising administering to said warm-blooded animals an amount of a polypeptide having human gamma interferon activity sufficient to treat primary cancers of pleura.

7 Claims, No Drawings

METHOD OF TREATING PRIMARY CANCERS OF THE PLEURA

STATE OF THE ART

Gamma interferon, in addition to its anti-viral and anti-proliferative properties, possesses a powerful immunomodulating activity which distinguishes it from alpha and beta interferons and it stimulates the phagocytary cells allowing, particularly the lysis of certain tumorous cells. The study of the tolerance of patients with terminal stage cancer to gamma interferon does not lead to the observation of remission from these cancers [Vadhan-Raj et al. (1986), J. Clin. Oncol., Vol 4 (2), p 137 to 146 or Van Der Burg et al. (1985), J. Biol. Resp. Mod., Vol. 4, p. 264 to 272] and notably in a patient suffering from mesothelioma having received an sub-cutaneous administration [Cox et al., Proceedings of AACR, Vol. 27, p. 191 March, 1986].

Primitive cancers of the pleura comprise essentially widespread mesotheliomas and more rarely sarcomas for which existing surgical, chemotherapy and radiotherapy treatments either on their own or combined does not show a recognized effectiveness. Therefore, malignant mesothelioma associated with exposure to asbestos has been suggested and confirmed [Antman, N. Eng. J. Med., (1980), Vol. 303, p. 200 to 202] in 10 to 70% of cases [Antman et al., Am. J. Med., (1980), Vol. 68, p. 356 to 362] and localized in the pleura, more frequently than in the peritoneum (ratio 2.5/1), leads to mortality in several months, in the absence of effective treatment.

The effectiveness of gamma interferon on various fresh human cancerous cells, according to the so-called "human tumor cloning system" test described by Hamburger et al., has been shown in Patent Application No. WO 87/05518, for example, on cancer colonies of the ovaries, lungs, kidney and notably on cancer colonies of the pleura. Following these observations, clinical studies have been conducted, for example in patients having cancer of the ovaries. However, the effectiveness of gamma interferon in vivo has not been observed either in intravenous administration, [Welander et al., Am. J Clin. Oncol (1988), Vol. 11, (4), p. 465 to 469), or according to a protocol using intraperitoneal administration [D'Acquisto et al., J. Clin. Oncol. (1988), Vol. 6, p. 689 to 695)].

Generally, it is admitted that the anti-cancerous action of gamma interferon requires its use in combination with other therapeutic agents [Saito et al., Cancer Chemother. Pharmacol. (1989), Vol. 19, p. 233 to 239].

OBJECTS OF THE INVENTION

It is an object of the invention to provide a novel method for the treatment of cancers of the pleura.

This and other objects and advantages of the invention will become obvious from the following detailed description.

THE INVENTION

The novel method of the invention of treating primary cancers of pleura in warm-blooded animals having said cancers comprises administering to said warm-blooded animals an amount of a polypeptide having human gamma interferon activity sufficient to treat primery cancers of pleura. Polypeptide having the activity of gamma interferon means natural human gamma, neutral interferon, human recombinant gamma interferon obtained by recombinant DNA technology, for example as that described by Gray et al., in Nature (1982), Vol. 295, p. 503 to 508 or in Patent No. EP 77,670, of alleles or of derivatives of these products such as described in Patent Application No. EP 161,504.

Primary cancers of the pleura include cancers such as pleural mesothelioma and sarcoma, generally characterized clinically by a pleural effusion and preferably, the cancer of the pleura is a mesothelioma pleural mesothelioma is generally characterized clinically by pains in the chest or respiratory difficulties associated with a pleural effusion and its diagnosis differentiates it from inflammatory pleurisy, primary lung cancer or metastases resulting from another primary cancer.

The use of human gamma interferon in a treatment results in an effectiveness of a response rate of about 30% in patients suffering from pleural mesothelioma, having possibly undergone exeresis surgery but not previous chemotherapy or radiotherapy treatment.

Preferably, the polypeptide having the activity of human gamma interferon is a pure recombinant gamma interferon such as a recombinant human gamma interferon, alleles or derivatives of the latter, as described above for which purification techniques are known for the preparation of high purity products. The gamma interferon is preferably that obtained starting with the E. Coli strain and containing 143 amino acids corresponding to the sequence of natural gamma interferon with a supplementary N-terminal methionine.

The specific activity of the products used is at least equal to $1 \times 10^7$ U/mg, determined according to the standard test by measurement of the anti-viral activity compared with the NIH standard on human Wish cells infected by the virus of the vesicular stomatitis and allows the administration of effective doses which are lower than the maximum dose tolerated expressed in milligrams of product. The method requires recombinant gamma interferons possessing a high degree of purity.

More particularly, the gamma interferon is administered intrapleurally at a dose of 10 to 50 million units by injection and more preferably the gamma interferon is administered at a dose of 40 million units.

The gamma interferon is administered in a repeated fashion on at least two non-consecutive days per week intrapleurally and more preferably the gamma interferon is administered in a repeated fashion for at least two months. The administered dose, the frequency of injection and the duration of the treatment varies as a function of the condition of the patient.

The gamma interferon is used in a pharmaceutical composition, preferably lyophilized in dispensing bottles of 0.5 to 2 milligrams of active ingredient and is reconstituted with distilled water for injection. The solution obtained is optionally immediately diluted using a solute, for example, 0.9% sodium chloride in the case of an intrapleural perfusion. In a preferred method of the invention, the gamma interferon has a specific activity of $2 \times 10^7$ U/mg, the dose is 40 million units per injection, the frequency of injection is twice a week and the duration of administration is 2 months for about 720 million units and 36 milligrams of gamma interferon administered in total by intrapleural perfusion. A maintenance treatment is then recommended for the patient by sub-cutaneous injection of gamma interferon under the conditions described above.

In the following examples, there are described several preferred embodiments to illustrate the invention. However, it should be understood that the invention is not intended to be limited to the specific embodiments.

EXAMPLE 1

Pharmaceutical Composition for Injection

A preparation for sub-cutaneous injection consisted of 1 mg of gamma interferon, 50 mg of excipient and 1 ml of sterilized water.

EXAMPLE 2

Pharmaceutical Composition for Injection

A preparation for intrapleural perfusion consisted of 2 mg of gamma interferon, 100 mg of excipient, 10 ml of sterilized water and 100 ml of 0.9% sodium chloride.

Clinical Study of the Treatment of Pleural Mesothelioma

The study included patients having a pleural mesothelioma which had been histologically confirmed, confined to the pleura, optionally extended to the lung, thorax or lymphatic ganglions (stages I, II or III according to Butchart's classification) and having had no previous treatment by chemotherapy or radiotherapy. The patients could possibly have had treatment by exeresis surgery and showed a recurrence of the illness.

The gamma interferon compositions of the invention were administered by injection of 40 million unit doses, that is 2 mg per injection, at the rate of 2 injections per week for 2 months by six hour intrapleural perfusion. The compositions of Example 2 were used. The patients who showed a total or partial response were then, when it is possible, put on a maintenance treatment by subcutaneous injection of 400 million units, this being 2 milligrams per injection, at the rate of 2 injections per week for as long as possible. The compositions described in Example I were used. The patients who showed a subsequent relapse or only either a partial response or a stabilization of the illness were treated again by intrapleural route as described above.

The tumorous lesions of the patients were evaluated before and at the end of treatment by measurement of the macroscopic lesions by thorax scanner and thorascopy. A histological confirmation was obtained by multiple biopsies of the areas previously attacked and random biopsies of the parietal and diaphragmatic pleura. On 13 re-evaluated patients, the following responses were obtained:

| PATIENT | SEX | AGE (years) | Histological type | STAGE | ENDOSCOPIC APPEARANCE | RESPONSE |
|---------|-----|-------------|-------------------|-------|-----------------------|----------|
| HO | M | 66 | Epithelial | 1A | Lymphangite | CR |
| RA | M | 48 | Epithelial | 1A | <5 mm nodules | CR |
| LL | M | 42 | Epithelial | 1A | <5 mm nodules | CR |
| FE | M | 58 | Epithelial | 1A | <5 mm nodules | CR |
| GO | M | 69 | Epithelial | III | | failure |
| PA | M | 70 | Epithelial | IIA | | failure |
| TR | M | 65 | Nonevaluable | IIA | | failure |
| GU | M | 65 | Nonevaluable | IIA | | failure |
| CH | M | 60 | Nonevaluable | IIA | | failure |
| FE | M | 54 | Mixed | III | | failure |
| RA | M | 68 | Epithelial | IIA | | failure |
| PE | M | 54 | Epithelial | IIA | | failure |
| THO | M | 41 | Epithelial | IIA | | failure |

The results show 4 complete responses (CR), this being a response rate of about 30%, including a complete macroscopic response but with a persistence of tumorous cells on histological examination.

Various modifications of the method of the invention may be made without departing from the spirit or scope thereof and it should be understood that the invention is intended to be limited only as defined in the appended claims.

What we claim is:

1. A method of treating primary cancers of pleura in warm-blooded animals having said cancers comprising administering interapleurally to said warm-blooded animals an amount of polypeptide having human gamma interferon activity with a specific activity at least equal to $1 \times 10^7$ U/mg sufficient to treat primary cancers of pleura.

2. The method of claim 1 wherein the cancer of pleura is a mesothelioma.

3. The method of claim 1 wherein the polypeptide is a pure recombinant gamma interferon having a specific activity of about $2 \times 10^7$ U/mg.

4. The method of claim 3 wherein the gamma interferon is administered intrapleurally at a dose of 10 to 50 million units per injection.

5. The method of claim 4 wherein the dose is about 40 million units per injection.

6. The method of claim 5 wherein the gamma interferon is administered repeatedly for at least two nonconsecutive days per week.

7. The method of claim 6 wherein the administration is effected for at least two months.

* * * * *

UNITED STATES PATENT AND TRADEMARK OFFICE
CERTIFICATE OF CORRECTION

PATENT NO. : 5,108,743
DATED : April 28, 1992
INVENTOR(S) : MAUD BRANDELY and DANIELLE LANDO It is certified that error appears in the above-identified patent and that said Letters Patent is hereby corrected as shown below:

| Col. | Line | |
|---|---|---|
| 1 | 68 | Cancel ",neutral gamma" |
| 2 | 9 | "Pleural" |
| 4 | 38 | Change "warm-blooded animals" to --humans-- |
| 4 | 39&40 | Cancel "interapleurally to said warm-blooded animals" and insert --interapleurally to said humans-- |

Signed and Sealed this

Twenty-sixth Day of April, 1994

Attest:

BRUCE LEHMAN

Attesting Officer

Commissioner of Patents and Trademarks